United States Patent
Stavrianos

(10) Patent No.: US 8,127,598 B2
(45) Date of Patent: Mar. 6, 2012

(54) PROCEDURE FOR DETERMINING THE PROPORTIONS OF COMPONENTS OF A FUEL MIXTURE

(75) Inventor: Dimitrios Stavrianos, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 638 days.

(21) Appl. No.: 12/272,454

(22) Filed: Nov. 17, 2008

(65) Prior Publication Data

US 2009/0139305 A1    Jun. 4, 2009

(30) Foreign Application Priority Data

Nov. 29, 2007    (DE) .......................... 10 2007 057 505

(51) Int. Cl.
  *G01M 15/00*    (2006.01)
  *G01N 33/22*    (2006.01)
  *F02M 7/06*    (2006.01)

(52) U.S. Cl. .................... 73/114.41; 73/61.43; 123/435

(58) Field of Classification Search ................. 73/61.41, 73/114.01, 114.41, 35.02, 61.43; 123/406.3, 123/435, 434, 704
See application file for complete search history.

(56) References Cited

U.S. PATENT DOCUMENTS

| | | | | |
|---|---|---|---|---|
| 4,905,649 | A | * | 3/1990 | Washino et al. ............... 123/435 |
| 5,499,607 | A | * | 3/1996 | Tomisawa ..................... 123/435 |
| 5,586,537 | A | * | 12/1996 | Tomisawa et al. ............ 123/435 |
| 2007/0246021 | A1 | * | 10/2007 | Takayanagi et al. .......... 123/497 |

FOREIGN PATENT DOCUMENTS

| | | |
|---|---|---|
| DE | 29 52 073 | 6/1981 |
| DE | 38 33 123 | 4/1989 |
| DE | 41 17 440 | 12/1991 |

* cited by examiner

*Primary Examiner* — John Fitzgerald
(74) *Attorney, Agent, or Firm* — Merchant & Gould P.C.

(57) ABSTRACT

A procedure for determining the proportion of components of a fuel mixture, which is boosted with a fuel pump, and a device for implementing the procedure are suggested. A measure for the power input of the fuel pump is detected, with whose aid the proportion of components of the fuel mixture is determined. By proceeding according to the invention a special sensor, which is susceptible to components of the fuel mixture can be waived.

10 Claims, 1 Drawing Sheet

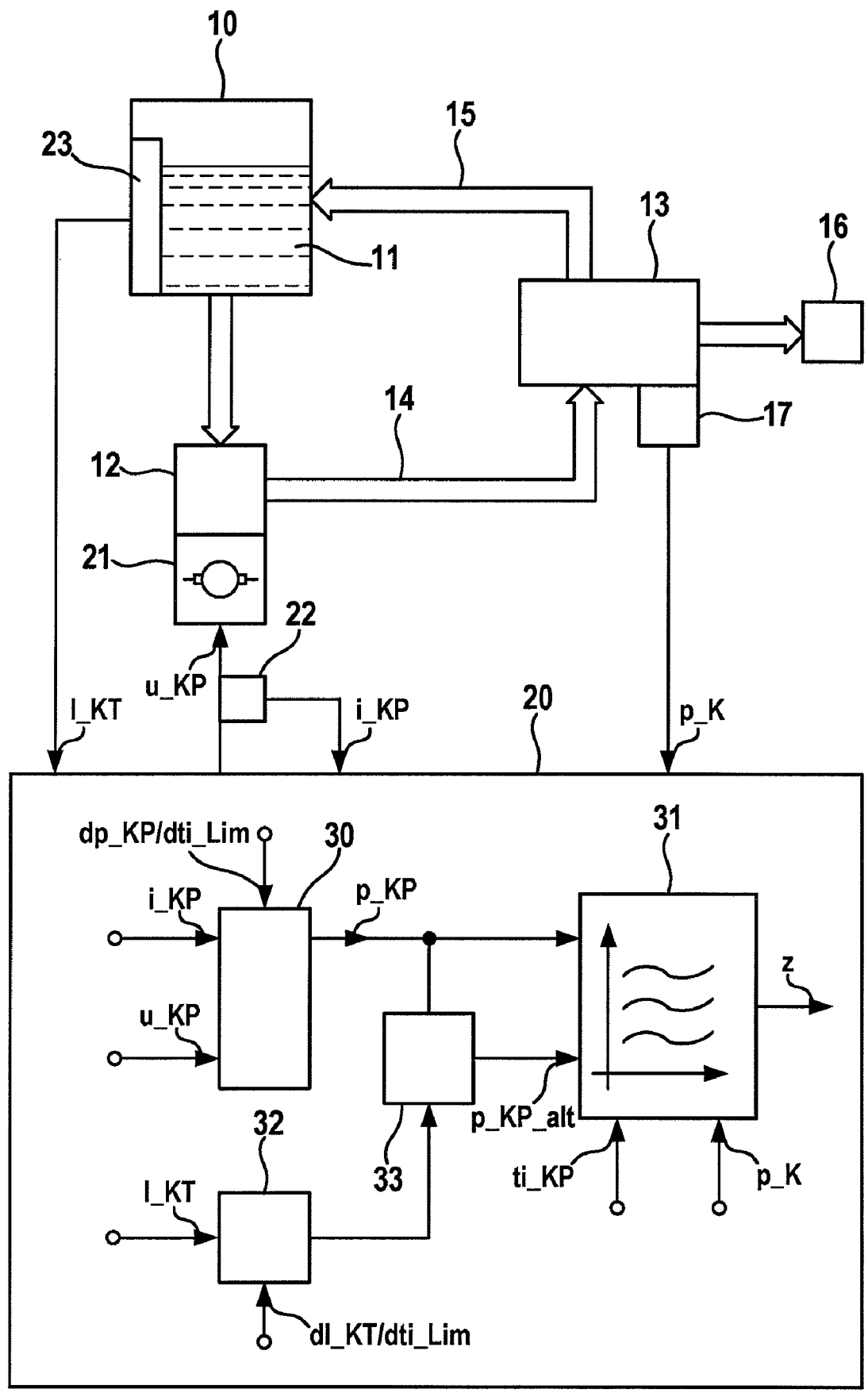

PROCEDURE FOR DETERMINING THE PROPORTIONS OF COMPONENTS OF A FUEL MIXTURE

TECHNICAL FIELD

The invention is based on a procedure for determining the proportions of components of a fuel mixture and a device for implementing the procedure according to the category of independent claims.

The invention especially concerns a procedure for determining the proportions of components of a fuel mixture from a first and at least a second fuel for operating a combustion engine.

Subject matter of the present invention is also a control unit program as well as a control unit program product.

BACKGROUND

Combustion engines based on Otto engines are generally operated with fuel consisting of hydrocarbons of fossil fuels on the basis of refined petroleum. Ethanol that is increasingly produced from re-growing natural resources (plants) or another alcohol is added to this fuel in different mixture ratios. In the United States and Europe a mixture of 70-85% ethanol and 15-30% gasoline are used under the trade name E85. The combustion engines are construed in such a way that they can be operated with pure gasoline as well as with mixtures up to E85; this is called 'flex-fuel-operation'.

For an economical operation with a low pollutant emission at a simultaneously high engine performance and good starting behavior the operating parameters in the flex-fuel-operation have to be adapted to the present fuel mixture. A stoichiometric air/fuel ratio is for example present at 14.7 weight proportions of air per proportion of gasoline, but an air percentage of 9 weight proportions has to be adjusted when using pure ethanol. Furthermore the ignition angle of the combustion engine has to be adjusted to the mixture proportions for an optimal combustion.

Due to the different evaporation characteristics of ethanol and gasoline different enhancement factors have to be predefined at the start of the combustion engine depending on the mixture proportion. The knowledge of the present fuel mixture proportion is therefore of extreme importance for the operation of the combustion engine.

DE 41 17 440 C2 describes a procedure for an adaptive adjusting of an air/fuel mixture for considering fuel characteristics during the operation of a combustion engine, which provides a lambda regulator, which emits a regulating factor RF, and which provides an adaptation integrator, which emits an adaptation factor AF with a variable adaptation speed, which influences not only the regulating factor RF but also the adjustment of the air/fuel mixture. Thereby a checking of whether the lambda-regulating-deviation-amplitude exceeds a first threshold is provided, and, if that is the case, the adaptation speed is adjusted to a higher value so long until a preset condition is fulfilled, according to which it is switched back to a low adaptation speed. The underlying procedure is known as fuel adaptation.

The fuel adaptation allows a trouble-free operation of combustion engines, which can be operated with different fuels. Thus the injection time has to be extended by over 40% for example at a change from gasoline to a fuel mixture of 85% ethanol and 15% gasoline, in order to get the same lambda values in the exhaust gas. This is based on the different air demand for a stoichiometric combustion.

According to the procedure that is described in DE 41 17 440 C2 a corresponding adaptation intervention is carried out therefore. Because a correction of the injection times and therefore of the adaptation intervention that is very strong compared to balancing ageing influences or manufacturing influences has to be undertaken at a fuel exchange, the adaptation speed is significantly increased at the suggested procedure during a recognized fuel exchange.

The mixture proportion of the injected fuel can be implied from the adaptation intervention and the therefore resulting injection time or the fuel amount that has been injected into the combustion engine, whereupon further operating parameters of the combustion engine can be adjusted to the present fuel mixture.

The disadvantage of the described procedure is that at a required adaptation intervention into the lambda regulation it can not be surely determined anymore, whether the intervention is required because of ageing drifts and tolerances or because of a change of the fuel mixture proportions, thus whether the adaptation intervention has to be carried out by the mixture—or the fuel-adaptation. A corresponding attribution can be made with a certain probability based on distinction criteria, as for example the speed of the change or a refueling detection or a knock tendency.

But a residual uncertainty remains. If the system has unlearned once, thus if a change of the fuel mixture proportion has been interpreted falsely as a tolerance or an ageing drift and thus balanced correspondingly by a mixture adaptation, the error can only be detected and reversed very difficultly afterwards. Referring to the fuel injection it does not matter, whether the adaptation is carried out by the mixture adaptation or the fuel adaptation.

When changing the fuel mixture proportions further measures, as for example an adaptation of the ignition angle or a start enhancement, are necessary besides the adaptation of the fuel amount that has been injected into the combustion engine. These measures are not implemented in the described misinterpretation.

Further procedures, which are known from the patent literature, allow a conclusion about different characteristics of the used fuel, among others due to different mixture proportions of fossil fuel and alcohols, and a corresponding adaptation of the operating parameters of the combustion engine.

Thus DE 29 52 073 A1 describes a procedure for optimizing the working cycle of a spark-ignited combustion engine, at which the drive data of the combustion engine, among others the actually relative angle position of the crankshaft (crank angle), is measured, send to an electronic control unit and then the ignition time and/or the injected fuel amount is correspondingly affected. In doing so it is provided to vary around an approximate threshold value of at least one of the variables of the ignition time and/or the injected fuel amount from working cycle to working cycle.

Besides the crank angle the currently indicated pressure or a variable that changes analogously with is furthermore measured. By doing so and by determining the piston position by the crank angle the averagely indicated pressure or an analogous variable is calculated for each work stroke. The result of the calculated value of the averagely indicated pressure is registered and subsequently consecutive values are compared to each other. Thereby the variation of the variable is terminated for each operating status of the combustion engine and the present value of the variable is registered, as soon as the averagely indicated pressure reaches a maximum value.

The procedure also allows among others, to balance deviations of control parameters in the controlling of the combustion engine, which originate from the use of different fuels, as for example methanol, ethanol and gasoline.

A device for detecting the fuel characteristics is known from DE 38 33 123 A1, whereby the air amount that has been sucked in by the combustion engine and the air/fuel proportion in the exhaust gas are measured, whereby a significant fuel injection amount is calculated on the basis of the sucked in air amount and whereby the amount of the fuel that has to be inject is regulated correspondingly to the air/fuel proportion.

The device is characterized by pressure detection means for detecting the internal cylinder pressure, crankshaft detection means for detecting the crank angle of the combustion engine and a control device, which receives signals from the pressure detection means and the crank angle detection means and which calculates an effective fuel value Q of the fuel in an ignition cycle on the basis of the internal cylinder pressure P (θ) at a crank angle θ in the compression- and expression-strokes of an ignition cycle, the crank angle and the cylinder capacity V(θ), and which determines an effective combustion value K or a lower fuel value Hu of the fuel, whereby the characteristics of the fuel are determined by using at least the effective combustion value K or the lower fuel value Hu or the proportion (Ti/Hu) of the duration Ti of a fuel injection impulse to the lower fuel value Hu.

It is the task of the invention, to provide a procedure, which allows the determination of the proportion of components of a fuel mixture.

SUMMARY

According to the invention the procedure for determining the proportion of components of a fuel mixture assumes that the fuel mixture is boosted by a fuel pump. It is provided that a measure for the power input of the fuel pump is detected and that the proportion of the components of the fuel mixture is determined with the aid of this measure.

According to the invention the procedure has the advantage that no separate sensor, which is susceptible to the individual components of the fuel mixtures, is necessary for determining the proportion of components of a fuel mixture.

Advantageous improvements and embodiments of the procedure according to the invention accrue form dependent claims.

One embodiment provides that the proportion of the components of the fuel mixture is determined in an operating status of the fuel pump that is approximately stationary. Thereby it is made sure, that non-stationary operating statuses are not influencing the determination of the proportion in a negative way.

Another embodiment provides that the proportion of the components of the fuel mixture is determined depending on the pressure of the fuel mixture that is boosted by the fuel pump. Thereby a dependency on the operating pressure of the boosted fuel mixture on to the power input of the fuel pump can be compensated if necessary.

An improvement of the procedure provides a reasonability test of the measure for the power requirement of the fuel pump related to a refueling of the fuel mixture.

A further embodiment provides that the operating current of an electric drive of the fuel pump is used as the measure for the power input of the fuel pump. As long as an electromotor is provided as the drive, a measure for the power input of the fuel pump can be thereby won very easily.

The device according to the invention for implementing the procedure concerns initially a control unit, which is customized for implementing the procedure.

Furthermore the device provides an electromotive drive of the fuel pump. In that case the operating current of the electromotive drive that is provided by a current sensor is used as a measure for the power input of the fuel pump.

The control unit preferably contains at least one electrical storage, in which the steps of the procedure are saved as a control unit program.

The control unit program according to the invention provides, that all steps of the procedure are implemented, when it runs in a control unit.

The control unit program product according to the invention with a program code that is saved on a machine readable medium implements the procedure, when the program runs in a control unit.

Further advantageous improvements and embodiments of the procedure accrue from further dependent claims. Embodiments of the invention are shown in the drawings and further explained in the following description.

DETAILED DESCRIPTION

The FIGURE shows a fuel tank 10 stockpiled with a fuel mixture 11, which contains at least two different main components. In the following the form of fuel mixture 11 shall contain gasoline and ethanol, whereby the mixture proportion can lie between 0% and 100%. The fuel mixture 11 is preferably provided for the fuel supply of a not further shown combustion engine.

The fuel mixture 11 is pumped by a fuel pump 12 for example into a closed circuit, which contains an inlet 14 that leads partially to a rail 13 and a return 15 that leads back from the rail 13 to the fuel tank 10. A fuel metering 16, which is realized for example as at least one fuel injection valve, is attached to the rail 13.

The fuel pressure in the rail 13 is detected by a pressure sensor 17 and provided as a pressure signal p_K to a control unit 20.

The fuel pump 12 is driven by a preferably electric drive 21. As long as an electric drive 21 is provided, the electromotor of the drive 21 is provided with an operating voltage u_KP. The operating current i_KP that flows through the electromotor of the drive 21 is detected by a current sensor 22 and provided to the control unit 20.

Furthermore the control unit 20 contains information about the filling level of the fuel mixture 11 in the fuel tank 10. A filling level sensor 23 provides a corresponding filling level signal 1_KT of the fuel mixture 11 in the fuel tank 10 to the control unit 20.

The initial point for determining the proportion of components of the fuel mixture 11, whereby at least two components exist, is the detection of the power input of the fuel pump 12. It has been proven, that a different drive input of the fuel pump 12 is required depending on the proportion z of the components of the fuel mixture 11. The different power input results from a change of the lubricating quality and the concentration of the fuel mixture 11 depending on the proportion z of the components of the fuel mixture 11. The proportion z of the components of the fuel mixture 11 can therefore be determined from a detected measure for the power input of the fuel pump 12.

The control unit 20 contains a power detection 30, which detects the power of the drive 21. As long as it is an electromotive drive 21, the electric power results as a measure for the power input of the fuel pump 12 by a multiplication of the operation voltage u_KP that is provided to the electromotor and the engine current i_KP that flows through the electromotor.

It is sufficient to provide at least one measure p_KP for the power of the fuel pump 12. As long as an electromotor is provided as the drive 21, the detection of only the operating current i_KP is already sufficient at a preset operating voltage u_KP for determining the measure p_KP for the drive power of the fuel pump 12. The operating voltage u_KP amounts to for example at least 12 V, which is for example provided by a motor vehicle battery.

So that the turn-on process of the fuel pump 12 and other non-stationary operating statuses have preferably no influence on the determination of the proportion z of the components of the fuel mixture 11, the measure p_KP for the power input is preferably determined in at least approximately stationary operating status of the fuel pump 12. Therefore the power detection 30 is for example provided with a power-modification-threshold (dp_KP/dti_Lim). The measure p_KP for the power of the fuel pump 12 is only provided, when the power-modification-threshold (dp_KP/dti_Lim) is not exceeded.

Alternatively an at least approximately stationary operating status of the fuel pump 12 can be detected from the pressure signal p_K. instead of the power-modification-threshold (dp_KP/dti_Lim) a pressure-modification-threshold has to be provided then. Furthermore an at least approximately stationary operating status of the fuel pump 12 can be determined alternatively from not further shown operating status of the combustion engine that is supplied with the fuel mixture 11. For this purpose the current default load status of the combustion engine and/or the engine speed of the combustion engine for example can be used for determining the presence of an at least approximately stationary operating status.

The measure p_KP for the drive power of the fuel pump 12 is used in a proportion-determination 31 for determining the proportion z of the components of the fuel mixture 11. The proportion-determination 31 can contain formulas, from which the proportion z results with the measure p_KP as an initial parameter. Preferably the proportion-determination 31 contains the proportion in tabular form in order to save computing power.

Based on the example that the fuel mixture 11 consisting of gasoline and alcohol contains ethanol, the power requirement of the fuel pump 12 increases with an increasing alcohol concentration. It has been shown experimentally that the power requirements of the fuel pump increases with an increasing alcohol concentration depending on the alcohol percentage of about 15%.

A reasonability test of the result of the proportion-determination 31 can be undertaken by considering the modification of the filling level in the fuel tank 10. A modification of the proportion z can be expected, when fuel is refueled. The control unit 20 preferably contains a filling-modification-evaluation 32, which compares the filling level signal 1_KT that is provided by the filling level sensor 23 with the filling-level-modification-threshold (dp_KP/dti_LIM). When refueling a modification of the filling level occurs within a short period of time, which signalizes the filling-modification-evaluation 32 with the provision of a storage signal s. The storage signal s is provided to a storage 33, which stores the determined measure p_KP for the power of the fuel pump 12 at a present storage signal s. The proportion-determination 31 is then provided for the previous measure p_KP_alt as well as the current measure p_KP and can thereupon carry out the reasonability test with the aid of a comparison. Especially a modification of the proportion z can be thereby confirmed, when it has been refueled at the same time.

The measure p_KP for the power of the fuel pump 12 or the electric power requirement of an electromotor in the drive 21 can depend on the pressure of the boosted fuel mixture 11. The pressure signal p_K, which is provided for the proportion-determination 31, can be used as a measure for the pressure.

It has been furthermore established that the measure p_KP for the power can depend on the fuel pump total operating time ti_KP. For this purpose it has to be considered, that usually a fuel filter is provided, which can be arranged for example in the fuel pump 12. It could be experimentally shown, that the measure p_KP for the power requirement of the fuel pump 12 increases with an increasing total operating time ti_KP of the entire system, which is reflected in the total operating time ti_KP of the fuel pump 12. The fuel pump total operating time ti_KP is therefore provided to the proportion-determination 31.

The pressure signal p_K as well as the fuel pump total operating time ti_KP can be considered in the proportion determination 31 by a deposit of different curve shapes depending on the parameter p_K or ti_KP.

The determined proportion z of the components of the fuel mixture 11 can especially be considered at the metering of fuel for operating a combustion engine. In order to adhere to a default air-fuel proportion for example, a higher metering of the fuel mixture is necessary at a fuel mixture 11 that consists for example of gasoline and alcohol at an increasing alcohol content.

The proportion z can furthermore be used for the reasonability test of the proportion of the components of the fuel mixtures 11 that has been determined differently.

Alternatively the proportion z can be determined for example by an intervention in a not further shown lambda regulator of a combustion engine, whereby the proportion z that has been obtained this way can be substantiated with the procedure that has been described here.

The invention claimed is:

1. A method of determining a proportion of components of a fuel mixture that is boosted with a fuel pump, the method comprising:
   detecting a measure for a power input of the fuel pump; and
   determining the proportion of a first component and a second component of the fuel mixture with the detected measure for the power input of the fuel pump, wherein the first component is gasoline and the second component is ethanol.

2. A method according to claim 1, further comprising determining the proportion of components of the fuel mixture in an operating status of the fuel pump that is at least approximately stationary.

3. A method according to claim 1, further comprising depending on an entire operating time of the fuel pump upon determining the proportion of components of the fuel mixture.

4. A method according to claim 1, further comprising depending on a pressure of the fuel mixture that is boosted by the fuel pump upon determining the proportion of components of the fuel mixture.

5. A method according to claim 1, further comprising undertaking a reasonability test of a measure for a power requirement of the fuel pump related to a refueling of the fuel mixture.

6. A method according to claim 1, further comprising using an operating current of an electric drive of the fuel pump as a measure for the power input of the fuel pump.

7. A device, comprising: a customized controller constructed and configured to determine a proportion of components of a fuel mixture that is boosted with a fuel pump, to detect a measure for a power input of the fuel pump; and to determine the proportion of a first component and a second component of the fuel mixture with the detected measure for the power input of the fuel pump, wherein the first component is gasoline and the second component is ethanol.

8. The device of claim 7, wherein the fuel pump comprises an electromotive drive, wherein an operating current of the electromotive is used as a measure for the power input of the fuel pump, and wherein the operating current is provided by a current sensor.

9. A computer-implemented method for determining a proportion of components of a fuel mixture that is boosted with a fuel pump, the computer-implemented method comprising: detecting a measure for a power input of the fuel pump; and determining the proportion of a first component and a second component of the fuel mixture with the detected measure for the power input of the fuel pump, wherein the first component is gasoline and the second component is ethanol.

10. A computer program product with a program code that is saved on a machine readable device and executed on a control unit for determining a proportion of components of a fuel mixture that is boosted with a fuel pump, the program code including instructions for detecting a measure for a power input of the fuel pump; and determining the proportion of a first component and a second component of the fuel mixture with the detected measure for the power input of the fuel pump, wherein the first component is gasoline and the second component is ethanol.

* * * * *